United States Patent
Choi et al.

(10) Patent No.: US 7,951,987 B2
(45) Date of Patent: May 31, 2011

(54) THERMAL-CRACKING METHOD OF HYDROCARBON

(75) Inventors: Jun-seon Choi, Daejeon (KR);
Byoung-gi Park, Jeollanam-do (KR);
Jin-do Kim, Daejeon (KR); Hyune-jung Ryu, Jeollanam-do (KR)

(73) Assignee: LG Chem, Ltd. (KR)

( * ) Notice: Subject to any disclaimer, the term of this patent is extended or adjusted under 35 U.S.C. 154(b) by 285 days.

(21) Appl. No.: 12/217,246

(22) Filed: Jul. 2, 2008

(65) Prior Publication Data
US 2009/0012340 A1    Jan. 8, 2009

(30) Foreign Application Priority Data

Jul. 5, 2007    (KR) .................. 10-2007-0067470

(51) Int. Cl.
C07C 4/06    (2006.01)

(52) U.S. Cl. .................. 585/651; 585/652; 585/653

(58) Field of Classification Search .......... 585/651–653; 502/308, 309
See application file for complete search history.

(56) References Cited

U.S. PATENT DOCUMENTS

| | | | |
|---|---|---|---|
| 3,520,656 A | 7/1970 | Meadows et al. | |
| 3,644,557 A | 2/1972 | Senes et al. | |
| 3,725,495 A | 4/1973 | Wrisberg et al. | |
| 3,969,542 A | 7/1976 | Tomita et al. | |
| 4,111,793 A | 9/1978 | Kolombos et al. | |
| 4,269,737 A * | 5/1981 | Grenoble et al. | 502/204 |
| 4,692,306 A | 9/1987 | Minet et al. | |
| 5,053,577 A | 10/1991 | Teller et al. | |
| 5,600,051 A | 2/1997 | Baker et al. | |
| 6,224,748 B1 | 5/2001 | Chang et al. | |
| 7,022,643 B2 * | 4/2006 | Yunoki et al. | 502/300 |
| 7,026,263 B2 | 4/2006 | Le Van Mao et al. | |
| 7,232,780 B2 | 6/2007 | Zhu et al. | |
| 7,288,691 B2 * | 10/2007 | Martin et al. | 585/652 |
| 2003/0180473 A1 | 9/2003 | Nishihara et al. | |
| 2005/0234283 A1 | 10/2005 | Xu et al. | |

(Continued)

FOREIGN PATENT DOCUMENTS

EP    0 212 320    3/1987

(Continued)

OTHER PUBLICATIONS

U.S. Appl. No. 12/154,656.

(Continued)

Primary Examiner — Tam M Nguyen
(74) Attorney, Agent, or Firm — Lerner, David, Littenberg, Krumholz & Mentlik, LLP

(57) ABSTRACT

The present invention relates to a thermal-cracking method of hydrocarbon using a hydrocarbon thermal-cracking apparatus including a tube type furnace having a radiation part for thermally cracking hydrocarbon feedstocks supplied together with steam and a convection part. A hydrocarbon thermal-cracking catalyst is packed in some or entire area of the tube placed in the radiation part of the tube type furnace, wherein the hydrocarbon thermal-cracking catalyst includes an oxide catalyst represented by $CrZr_jA_kO_x$ (wherein, $0.5 \leq j \leq 120$ and $0 \leq k \leq 50$, A is a transition metal, and x is a number corresponding to the atomic values of Cr, Zr, and A and the numbers of j and k). Therefore, it is possible to improve yield and selectivity of olefin, reduce fuel consumption due to an excellent heat transfer efficiency and extend decoking interval by reduced production of coke deposited to an inside wall of a tube, in steam cracking of hydrocarbon for producing olefin.

11 Claims, 3 Drawing Sheets

U.S. PATENT DOCUMENTS

| | | |
|---|---|---|
| 2005/0245387 A1 | 11/2005 | Zhu et al. |
| 2008/0081008 A1 | 4/2008 | Choi et al. |

FOREIGN PATENT DOCUMENTS

| | | |
|---|---|---|
| KR | 20020048774 A | 6/2002 |
| KR | 20030083924 A | 11/2003 |
| KR | 20040016552 A | 2/2004 |
| KR | 20040101868 A | 12/2004 |
| KR | 20050016708 | 2/2005 |
| KR | 20060055366 A | 5/2006 |
| RU | 1011236 | 1/2000 |
| WO | 2004105939 | 12/2004 |

OTHER PUBLICATIONS

Takita et al. "Catalytic decomposition of CFCs", Catalysis Surveys from Japan 2 (1998) 165-173.

Sohn et al. "Surface Characterization of Chromium Oxide-Zirconia Catalyst" Langmuir 1993 9, 126-131.

Office Action and Response from U.S. Appl. No. 11/902,665 dated May 11, 2010.

U.S. Appl. No. 11/902,665, filed Sep. 24, 2007.

Gates, "Catalysis" in Kirk-Othmer Encyclopedia of Chemical Technology, John Wiley, 2002, published on-line Aug. 16, 2002.

* cited by examiner

THERMAL-CRACKING METHOD OF HYDROCARBON

This application claims the benefit of the filing date of Korean Patent Application No. 10-2007-0067470 filed on Jul. 5, 2007 in the Korean Intellectual Property Office, the disclosure of which is incorporated herein in its entirety by reference.

TECHNICAL FIELD

The present invention relates to a thermal-cracking method of hydrocarbon, more precisely, a thermal-cracking method of hydrocarbon by packing a specific catalyst within a radiation part of a tube type furnace, for thermally cracking hydrocarbon feedstock, such as naphtha, ethane and the like, supplied together with steam to produce $C_4$ or lower light olefin, particularly ethylene and propylene.

BACKGROUND ART

Ethylene and propylene are important fundamental raw materials for petrochemical products and are mainly produced by thermal-cracking of paraffin-based hydrocarbons such as natural gases, naphthas and gas oils at a high temperature of at least 800° C. in the presence of steam. In general, gaseous raw materials include ethane, propane, butane and a mixture thereof and liquid raw materials include naphthas, kerosenes, gas oils and a mixture thereof. Besides olefins as major product, a large amount of byproduct including hydrogen, methane, acetylene, carbon monoxide, carbon dioxide or the like is produced. A diluent, which is mixed with the hydrocarbon and then put into a heating furnace, is supplied to build the reaction condition for obtaining a desired product. The diluent lowers a partial pressure of the hydrocarbon reactant to reduce the amount of the byproduct such as hydrogen or methane and restrict an amount of coke produced in the tube type furnace to the minimum amount. Steam is preferred as the diluent.

The tube type furnace includes a radiation part for heating the reaction mixture to thermally crack the reaction mixture by radiant heat transfer resulted from burning of fuel such as gas oil or natural gas in a burner and a convection part for receiving supplied reaction raw materials and preheating the reaction raw materials by convective heat transfer resulted from the burned gas exhausted from the radiation part. At this time, the reaction raw materials make a stream flowing rapidly in a circular tube arranged in parallel or in a coil shape from the convection part to the radiation part of the furnace. Heat generated by the burning of the fuel in the burner placed in the radiation part of the furnace is transferred to the reaction stream through the circular tube, thus resulting in generation of the thermal-cracking reaction. After that, the cracked gas is rapidly cooled in a heat exchanger.

In general, a temperature of the hydrocarbon stream at an outlet of the convection part of the furnace is set in the range of 450~650° C., a temperature (COT; coil outlet temperature) of the hydrocarbon stream at an outlet of the radiation part of the furnace is set in the range of 750~950° C. and a residence time of the gaseous hydrocarbon in the tube of the radiation part is set in the range of about 0.01~1.5 seconds, although they are set differently depending upon the kind of the hydrocarbon supplied to the hydrocarbon thermal-cracking furnace. Also, although a diameter and a length of the tube may vary as the design of the thermal-cracking furnace, the tube has generally an inside diameter of 25~200 mm and a length of 8~100 m. Such tube can resist high temperature and is made of high temperature thermostable metal containing high content of nickel, iron and chromium. Example of the mainly used thermostable metal includes Incoloy 800, Inconel 600, HK-40, Cr—Mo steel alloy, 304 SS and 316 SS. However, the component such as nickel or iron is well known as a catalyst which causes formation of coke. Since the hydrocarbon thermal-cracking process should be performed in a very short time and a sufficient amount of heat for thermal-cracking should be supplied in order not to cause generation of undesirable side reaction through the thermal-cracking in the radiation part, the hydrocarbon thermal-cracking process consumes very much energy.

During the thermal-cracking of the hydrocarbon, carbon or similar deposits is generated and deposited to inside wall of the tube, which is an important limitation factor in an operation of the thermal-cracking furnace. Such deposits reduce an effective sectional area to cause an increase in a differential pressure between the circular tubes of the furnace and heat exchanger, thereby reducing yield of the light olefins. The deposits of carbon component act as a good insulator, which may prevents the heat transfer from the furnace to the reaction stream and thus increases more the fuel consumption. Also, uniformity of the heat transfer may be reduced, and therefore the production of the deposits may be accelerated and properties of the tube material may be deteriorated. Accordingly, when a temperature of the tube is increased to at least a predetermined temperature during continuous operation of the furnace at a reference performance, the operation of the furnace should be temporarily paused to perform removal of the carbon deposits. The removal of the carbon component deposits in the furnace and heat exchanger is largely divided into a physical cleaning and a decoking that removes the carbon component deposits by burning the carbon component deposits using steam/air. This carbon deposit removal takes a week to three months depending upon a deposition speed of the carbon component deposits in the thermal-cracking furnace and the heat exchanger. Although this carbon deposit removal is necessary to maintain the apparatus performance, it is advantageous in aspects of productivity and economy that the interval of the carbon deposit removal is as long as possible. There is therefore a need for a thermal-cracking apparatus with reduced fuel consumption by improved heat transfer efficiency, reduced production of the coke deposited within the tube and a long decoking interval.

Meanwhile, in order to increase yield of ethylene and propylene in a steam cracking of hydrocarbon, it is required higher conversion rate of hydrocarbon or higher selectivity of olefin. However, the steam cracking alone has limitations in increasing the hydrocarbon conversion rate or the olefin selectivity. In this regard, there have been suggested various methods capable of increasing the olefin yield.

As a method for increasing the yield of ethylene and propylene in the hydrocarbon steam cracking, there has been suggested a catalytic steam cracking. U.S. Pat. No. 3,644,557 discloses use of a catalyst including magnesium oxide and zirconium oxide; U.S. Pat. No. 3,969,542 discloses use of a catalyst consisting essentially of calcium aluminate; U.S. Pat. No. 4,111,793 discloses use of a zirconium oxide-supported manganese oxide catalyst; European Patent Publication No. 0212320 A2 discloses use of a magnesium oxide-supported iron catalyst; and U.S. Pat. No. 5,600,051 discloses use of a catalyst including barium oxide, alumina, and silica. Also, WO2004/105939 discloses use of a catalyst including potassium magnesium phosphate, silica and alumina. However, use of these catalysts is known to increase the olefin yield by action of the catalyst material as a heating medium in the hydrocarbon steam cracking and thus has a problem that an increase in the yield of olefins is insignificant as compared to use of an inactive carrier.

Russian Patent No. 1,011,236 discloses a boron oxide-grafted potassium vanadate catalyst supported on an alumina carrier. However, in use of the alkaline metal oxide or potassium vanadate catalyst, an increase in the olefin yield due to the catalyst is small and inevitable losses are also generated at high temperature for the hydrocarbon thermal-cracking. In other words, the catalyst may be present in a liquid phase in a hot reactor due to its low melting point and catalyst components may therefore be dissipated by volatilization with time due to fast flow of reaction gases.

U.S. Pat. No. 7,026,263 discloses use of a hybrid catalyst including molybdenum oxide, alumina, silica, silicalite and zirconium oxide. Such catalyst has an advantage that a reaction can be performed at a low reaction temperature, but it is difficult to apply the catalyst directly or indirectly into existing process since the catalyst is used at a very low hydrocarbon feed rate. Also, thermal stability of the catalyst is significantly decreased at a reaction temperature of at least 700~800° C. and loss of the catalytic activity is thus resulted.

Further, since existing thermal-cracking process is performed at high reaction temperature and high hydrocarbon linear velocity and is accompanied with a large amount of coke generation, it is necessary to burn the generated coke at a high temperature. In order that the catalyst can be used for a long time in such severe operation condition, the catalyst should be stable against thermal/physical deformation. The abovementioned prior arts have a problem that they are weak to the thermal/physical deformation or stability thereof is not verified.

Accordingly, when considering an economic aspect of the steam cracking of hydrocarbon or in order to avoid a process complexity, there is required a catalyst with more significantly increased light olefin yield than that in the inactive carrier and excellent thermal/mechanical stability at a high temperature.

DISCLOSURE OF THE INVENTION

It is an object of the present invention, to solve the above problems, to provide a thermal-cracking method of hydrocarbon which is capable of improving yield and selectivity of olefin, reducing fuel consumption due to an excellent heat transfer efficiency and extending decoking interval by reduced production of coke deposited to an inside wall of a tube, in steam cracking of hydrocarbon for producing olefin.

The above objects of the present invention can be achieved by the following embodiments of the present invention.

To achieve the object of the invention, the present invention provides a thermal-cracking method of hydrocarbon. The thermal-cracking method of hydrocarbon according to the present invention is performed in a tube type furnace including a radiation part for thermally cracking hydrocarbon feedstocks supplied together with steam and a convection part. At this time, a hydrocarbon thermal-cracking catalyst is packed, in some or entire area of the tube placed in the radiation part of the tube type furnace, wherein the hydrocarbon thermal-cracking catalyst includes an oxide-catalyst represented by $CrZr_jA_kO_x$ (wherein $0.5 \leq j \leq 120$ and $0 \leq k \leq 50$, A is a transition metal, and x is a number corresponding to the atomic values of Cr, Zr, and A and the numbers of j and k). Preferably, the hydrocarbon thermal-cracking catalyst is formed in such a manner that the oxide catalyst is mixed with or supported on a carrier. More preferably, the oxide catalyst of the hydrocarbon thermal-cracking catalyst is included in a range of 0.5 to 50% by weight, based on total weight of the oxide catalyst and the carrier. Also, the hydrocarbon thermal-cracking catalyst, preferably, has a density of 0.5 to 3.5 $g/cm^3$, a surface area of up to 50 $m^2/g$ and a compressive strength of at least 1000N.

According to the thermal-cracking method of the present invention, it is possible to accomplish such a heat transfer efficiency that a cracked gas temperature is at least 820° C. when a tube metal temperature is set 1020° C. at an outlet of the radiation part of the tube type furnace.

According to the thermal-cracking method of the present invention, it is also possible to shorten a residence time of the supplied hydrocarbon in the tube of the radiation part 20 to 40% compared with when packed with no hydrocarbon thermal-cracking catalyst, in such a condition that conversion rate of the supplied hydrocarbon and yield of produced $C_4$ or lower light olefin when 30% of the tube of the radiation part is packed with the hydrocarbon thermal-cracking catalyst are maintained the same as when packed with no hydrocarbon thermal-cracking catalyst.

According to the thermal-cracking method of the present invention, it is also possible to obtain the same performance as conversion rate of the supplied hydrocarbon and yield of produced $C_4$ or lower light olefin obtained when the tube metal temperature at the outlet of the radiation part packed with no hydrocarbon thermal-cracking catalyst is 1020° C., in more relieved condition, i.e. in such a condition that the tube metal temperature at the outlet of the radiation part is 980° C.

According to the thermal-cracking method of the present invention, a loss of the performance indicated by the conversion rate of the hydrocarbon and the yield of $C_4$ or lower light olefin is 1 to 5% after two to five times repetition of performing continuously the thermal-cracking for 120 hours in the state that the cracked gas temperature is 800° C. at the outlet of the radiation part and then performing decoking operation in the presence of steam and air.

In an embodiment of the present invention, a production amount of the coke is indirectly calculated by determining the amount of carbon dioxide generated when the deposited coke is burned in the decoking operation. Less production of coke was confirmed from less production of carbon dioxide, compared with when the hydrocarbon thermal-cracking catalyst is not packed, and slow coke deposition speed results in excellent operation efficiency.

According to the thermal-cracking method of present invention, tube material temperature at the outlet of the radiation part could be lowered from 1020° C. to 980° C., the residence time of the hydrocarbon in the tube of the radiation part could be reduced 30%, lowering in the performance during two to five times repetition of 120 hours continuous operation and subsequent decoking could be maintained 1 to 5%, and the coke deposition speed in above condition was shown to be lower than when the hydrocarbon thermal-cracking catalyst is not packed.

Hereinafter, the present invention is described in detail.

To begin with, in a viewpoint of a hydrocarbon thermal-cracking catalyst used in the present invention, the present inventors confirmed that using an oxide containing Cr and Zr, or an oxide Cr, Zr and a transition metal, particularly one or more metal components selected from the group consisting of Ti, Nb, Mo, V, Co, Ni, W, Fe and rare earth metals results in increasing yield of light olefin based on the excellent catalytic activity, less inactivation by coke, and no deformation due to the thermal/physical stability at high temperature, compared with the prior art, and thus can overcome the problems of the prior art such as low hydrocarbon cracking activity and low yield of the light olefins, and therefore completed the present invention.

Two forms of the hydrocarbon steam cracking catalysts may be used in an apparatus of the present invention. One is a hybrid catalyst formed by mixing and sintering catalyst powder of an oxide represented by $CrZr_jA_kO_x$ with a carrier powder and the other is a hybrid catalyst formed by supporting catalyst powder of the oxide represented by $CrZr_jA_kO_x$ on a carrier.

The hydrocarbon steam cracking catalyst of the present invention is characterized by containing a catalyst component represented by the following formula 1.

$$CrZr_jA_kO_x \qquad \text{[Formula 1]}$$

Wherein, $0.5 \leqq j \leqq 120$, preferably $5 \leqq j \leqq 90$ and more preferably $70 \leqq j \leqq 90$, and $0 \leqq k \leqq 50$, preferably $5 \leqq k \leqq 30$, and more preferably $15 \leqq k \leqq 28$, A is a transition metal, and x is a number corresponding to the atomic values of Cr, Zr, and A and the numbers of j and k.

In formula 1, A contains one or more metal components selected from the group consisting of Ti, Nb, Mo, V, Co, Ni, W, Fe and rare earth metals.

The hydrocarbon steam cracking catalyst of the present invention is characterized by containing a catalyst component represented by the following formula 2 in which k of formula 1 is 0.

$$CrZr_jO_x \qquad \text{[Formula 2]}$$

Wherein, $0.5 \leqq j \leqq 120$, preferably $5 \leqq j \leqq 90$ and more preferably $70 \leqq j \leqq 90$, and x is a number corresponding to the atomic values of Cr and Zr, and the number of j.

When the catalyst of the present invention is used for hydrocarbon steam cracking, the reaction yield is increased, selectivity of light olefin, particularly propylene is improved and thermal stability is also improved.

The hydrocarbon steam cracking catalyst of the present invention may be prepared by the following method. The preparation method includes the steps of (a) preparing an aqueous solution by mixing a Cr containing compound and a Zr containing compound or a Cr—Zr containing compound with water; (b) preparing a slurry by coprecipitation after adding ammonia water to the prepared aqueous solution; (c) reflux-heating or hydrothermal treating the prepared slurry; (d) preparing an oxide catalyst represented by the formula 1 or 2 by filtering, drying and sintering the slurry of step (c); (e) preparing a hybrid catalyst by mixing and sintering the prepared powder of the oxide catalyst and powder of a carrier; (f) molding the hybrid catalyst; and (g) sintering the molded hybrid catalyst.

In step (a), an aqueous solution is prepared by mixing a metal compound with water.

The Cr containing compound and Zr containing compound or Cr—Zr containing compound above can be salts such as sulfates, nitrates, oxalates, halides or chlorides and particularly nitrates are more preferred.

The Cr containing compound and Zr containing compound or Cr—Zr containing compound can be mixed with the third metal compound. At this time, the third metal compound is one or more metal components selected form the group consisting of Ti, Nb, Mo, V, Co, Ni, W, Fe and rare earth metals, and Ti, Ni and rare earth metals are preferred and Ti and Y are more preferred.

The Cr containing compound and Zr containing compound or Cr—Zr containing compound can additionally include the third metal compound which is one or more metals selected from the group consisting of Ti, Nb, Mo, V, Co, Ni, W, Fe and rare earth metals, and Ti, Ni, and rare earth metals are preferred and Ti and Y are more preferred.

The third metal compound herein can be salt, acid, oxide, hydroxide or alkoxide. If a metal component of the third metal compound is alkoxide precursor, alkoxide will be hydrolyzed in water to precipitate a solid salt, in that case a strong acid such as nitric acid can be added to dissolve the solid.

The metal component of the third metal compound can be dissolved in water and then mixed with Cr and Zr aqueous solutions, or can be dissolved in water together with Cr and Zr precursors.

The aqueous solution above can be heat-stirred for at least one hour at 40 to 80° C., preferably at 60 to 70° C., to be a complete mixture.

In step (b), a slurry is prepared by adding ammonia water to the aqueous solution of step (a) with regulating pH to 7 to 9, preferably 8 to 8.5, for coprecipitation.

In step (c), the slurry of step (b) is reflux-heated at the same temperature set at step (a) for at least 12 hours or hydrothermal-treated by autoclave at 60 to 150° C.

In step (d), a catalyst is prepared by filtering, drying and firing the slurry of step (C).

It is preferred to dry the slurry at 120° C. for at least 2 hours.

It is preferred to fire the slurry at 750-1600° C. for at least 4 hours. When the slurry is prepared in the above temperature, sintering is not rapidly induced, protecting catalytic activity from being lost.

In step (e), the powder of the oxide catalyst component represented by formula 1 or 2 and prepared in step (d) is mixed and sintered with powder of a carrier. For the hydrocarbon steam cracking, it is preferred to mix 0.5 to 50% by weight, based on total weight of the hybrid catalyst, of the oxide catalyst component. If the mixed oxide catalyst component is less than 0.5% by weight, the hybrid catalyst is hard to serve as a catalyst. On the other hand, if the mixed oxide catalyst component is more than 50% by weight, the strength of the catalyst becomes weak. A binder may be additionally mixed in the step of mixing the oxide catalyst component and the carrier.

Conventional carriers such as α-alumina, silica, silica-alumina, zirconium oxide, magnesium oxide, magnesium aluminate, calcium aluminate, silicon carbide, aluminum titanate and zeolite can be used herein. At this time, a carrier containing silicon carbide is more preferred. When silicon carbide is used as the carrier, silicon and carbon which are precursors of silicon carbide may be mixed with the oxide catalyst component. In this case, silicon and carbon will be converted into silicon carbide through the sintering process of following step (g).

In step (f), the hybrid catalyst of step (e) is formed into a specific shape. The hybrid catalyst is formed into a specific shape by a compression molding or an extrusion molding.

In step (g), the product of step (f) having the specific shape is sintered. The product of step (f) having the specific shape is downsized in volume through the sintering process to be prepared into a hybrid catalyst having desired size, density and surface area. It is preferred to sinter the product of step (f) for at least two hours at a temperature of at least 1200° C.

Preferably, the completely sintered hybrid catalyst has a density of 0.5 to 3.5 g/cm³, a surface area of up to 50 m²/g and a compressive strength of at least 1000N.

Another method for preparing the hydrocarbon steam cracking catalyst of the present invention includes the steps of (a) preparing an aqueous solution by mixing a Cr containing compound and a Zr containing compound or a Cr—Zr containing compound with water; (b) impregnating a carrier with the prepared aqueous solution; and (c) preparing a hybrid catalyst containing an oxide component by sintering the impregnated carrier. Therefore, a supported catalyst, i.e. a hybrid catalyst, supported with a catalyst component of the oxide represented by formula 1 or 2.

In step (a), an aqueous solution is prepared by mixing a metal compound with water.

The Cr containing compound and Zr containing compound or Cr—Zr containing compound above can be salts such as sulfates, nitrates, oxalates, halides or chlorides and particularly nitrates are more preferred.

The Cr containing compound and Zr containing compound or Cr—Zr containing compound can be mixed with the third metal compound. At this time, the third metal compound is one or more metal components selected form the group consisting of Ti, Nb, Mo, V, Co, Ni, W, Fe and rare earth metals, and Ti, Ni and rare earth metals are preferred and Ti and Y are more preferred.

The Cr containing compound and Zr containing compound or Cr—Zr containing compound can additionally include the third metal compound which is one or more metals selected from the group consisting of Ti, Nb, Mo, V, Co, Ni, W, Fe and rare earth metals, and Ti, Ni, and rare earth metals are preferred and Ti and Y are more preferred.

The third metal compound herein can be salt, acid, oxide, hydroxide or alkoxide. If a metal component of the third metal compound is alkoxide precursor, alkoxide will be hydrolyzed in water to precipitate a solid salt, in that case a strong acid such as nitric acid can be added to dissolve the solid.

The metal component of the third metal compound can be dissolved in water and then mixed with Cr and Zr aqueous solutions, or can be dissolved in water together with Cr and Zr precursors.

The aqueous solution above can be heat-stirred for at least one hour at 40 to 80° C., preferably at 60 to 70° C., to be a complete mixture.

In step (b), a carrier supported with catalyst precursor material is prepared by impregnating (supporting) a carrier with the aqueous solution by incipient wetness impregnation or liquid-phase impregnation and drying the impregnated carrier at 120° C. for at least 10 hours.

It is preferred to calcine the carrier at 800 to 1400° C. for at least 6 hours.

For the hydrocarbon steam cracking, it is preferred for the calcined hybrid catalyst to contain 0.5 to 30% by weight, based on total weight of the hybrid catalyst, of the oxide catalyst component. If the content is less than 0.5% by weight, a catalytic effect may be insufficient. On the other hand, if it is more than 30% by weight, a catalytic effect corresponding to the content may not be obtained.

Conventional carriers such as α-alumina, silica, silica-alumina, zirconium oxide, magnesium oxide, magnesium aluminate, calcium aluminate, silicon carbide, aluminum titanate and zeolite can be used herein. At this time, a carrier containing silicon carbide having a compressive strength of at least 1000N is more preferred.

With the thermal-cracking method of hydrocarbon of the present invention including packing of the abovementioned hydrocarbon thermal-cracking catalyst, it is possible to improve the conversion rate of hydrocarbon and yield of $C_4$ or lower light olefin, as well as to accomplish improvement in operation efficiency of an furnace, such as reduced fuel consumption due to excellent heat transfer efficiency, reduced production of the coke deposited within the tube of the furnace or on the catalyst and resultant extension of decoking interval. Hereinafter, the light olefin indicates $C_4$ or lower light olefin, particularly ethylene and propylene.

FIGS. 1 to 3 illustrate examples of the thermal-cracking furnace for performing thermal-cracking method of hydrocarbon according to the present invention, in which the tube of the radiation part thereof is packed with the hydrocarbon thermal-cracking catalyst.

Referring first to FIG. 1, a thermal-cracking furnace 1 for applying the thermal-cracking method of hydrocarbon according to the present invention is a tube type furnace 100. The tube type furnace 100 includes a convection part 10 for preheating hydrocarbon feedstocks, such as naphtha or ethane, inputted therein together with steam, to a temperature not causing the thermal-cracking, a radiation part 20 for heating reaction stream to a temperature causing the thermal-cracking to perform the thermal-cracking, and a burner 30 placed in the radiation part 20 and heating the reaction stream to the reaction temperature. Also, tubes 11 and 21 serving passages for the reaction stream are continuously disposed within the tube type furnace 100. The reaction stream is thermally cracked in the tube 21 of the radiation part 20 to form cracked gas, which is rapidly cooled in a heat exchanger 200 as soon as the cracked gas is discharged from the radiation part 200. The thermal-cracking method of hydrocarbon according to the present invention includes packing the entire tube 21 of the radiation part 20 with the hydrocarbon thermal-cracking catalyst. The catalyst-packed area is shown by short dotted line in FIG. 1. In the apparatus in FIG. 1, the entire tube of the radiation part is packed with the catalyst is packed. At this time, the hydrocarbon thermal-cracking catalyst can be the catalyst described in above, and the hybrid catalyst formed by sintering after mixing the oxide catalyst powder and the carrier powder is preferred in aspects of economy and catalytic strength. Herein, silicon carbide is particularly preferred for the carrier.

In order to prevent a large pressure difference from being generated when packing the catalyst according to the method of the present invention, the catalyst formed in an annular shape can be packed so that the reaction stream passes therethrough. FIG. 1 shows that this cylindrical catalyst 22 is packed. In a typical example, the catalyst formed in a shape not generating the large pressure difference can be packed so that the reaction stream passes therethrough. It is preferred to be shaped in a raschig ring, a partition ring, a lessing ring and a foam.

According to the present invention, with respect to a same tube metal temperature (TMT) at an outlet of the tube of the radiation part, the temperature of the cracked gas in the reaction stream can be maintained higher than the temperature of the cracked gas in the case packed with no catalyst. When the TMT at the outlet of the tube of the radiation part is maintained at 1020° C., while the cracked gas temperature is 780° C. in the case packed with no catalyst, the cracked gas temperature can be maintained at 820° C. in the apparatus of the present invention. High heat transfer efficiency is exhibited in the method of the present invention, and this is because packing of the catalyst increases heat transfer efficiency by radiant heat as well as heat transfer efficiency to the reaction stream therethrough by increased surface area in contact with the reaction stream and the catalyst can therefore act as an excellent heat transfer medium.

Although tube material is not particularly limited as long as it has excellent thermal resistance and thermal conductivity, Incoloy 800, Inconel 600, HK-40, Cr—Mo steel alloy, 304 SS and 316 SS are preferred among the abovementioned heat resistant metals containing high content of nickel, iron and chromium.

FIG. 2 illustrates that a rear end portion of the radiation part is packed with the catalyst and FIG. 3 illustrates that a front end portion of the radiation part is packed with the catalyst. The area to be packed with the catalyst can be selected in consideration of performance improvement index such as improvement in the light olefin yield by catalyst activity, reduction in fuel consumption according to heat transfer effect, reduction in coke production amount and extension of decoking interval, and cost paid for the performance improvement, for example cost for use and packing of the catalyst and internal or external modification of the thermal-cracking apparatus according to pressure variation due to the packing of the catalyst.

According to the thermal-cracking method hydrocarbon, (a) improvement in the yield and selectivity of light olefin with increase in the thermal-cracking efficiency by the catalyst, (b) reduction in the fuel consumption with increase in heat transfer effect, (c) reduction in production of the cokes to be deposited onto the inside wall of the tube, and (d) extension of decoking interval can be achieved.

For example, (a), (b), (c) and (d) of the abovementioned effects can be achieved when the catalyst is packed in the entire of the radiation part as shown in FIG. 1. This is because, compared with the case without catalyst, packing the catalyst in the entire of the radiation part can improve the performance indicated by the conversion rate of hydrocarbon and yield of light olefin at the same TMT and, on the other hand, can lower the TMT required to obtain the same performance.

Also, for example, (b), (c) and (d) of the abovementioned effects can be particularly achieved when packing the rear end portion of the radiation part with the catalyst as shown in FIG. 2. In other words, amounts of the coke production and coke deposition are increased with increasing temperature as goes to the rear end portion of the radiation part, and packing the rear end portion of the radiation part with the catalyst according to the present invention and operating in the same operation condition as the case packed with no catalyst can decrease the production of the coke, to be deposited onto the inside wall of the tube, which occurs concentratively in the rear end portion of the radiation part.

Also, for example, (a) and (b) of the abovementioned effects can be particularly achieved when packing the front end portion of the radiation part with the catalyst as shown in FIG. 3. This can be achieved in such a condition that the temperature of the radiation part is properly lowered compared with the case packed with no catalyst. The thermal-cracking can be performed due to the catalytic activity even at a somewhat lowered temperature at the front end portion of the radiation part packed with the catalyst and can be additionally performed at the rear end portion of the radiation part. Thermal-cracking efficiency can be improved at the front end portion of the radiation part by the catalytic activity while thermal-cracking is performed at the somewhat lowered temperature [effect (a)], and the fuel consumption can be reduced since reaction temperature is somewhat lowered as a whole [effect (b)].

Accomplishment of the effects aimed by the present invention described above and conditions for accomplishing the effects are relative. In the present invention, a particularly aimed effect can be set by changing variously the operation condition of the thermal-cracking furnace. In the cast of packing the entire radiation part with the catalyst as shown in FIG. 1, operating in the same operation condition as the apparatus packed with no catalyst (COT at the outlet of the radiation part are maintained at the same) can accomplish reduction in production of the cokes and extension of the decoking interval due to the catalytic activity as well as improvement in olefin yield. In addition, it is possible to accomplish reduction in fuel consumption since it is possible to lower the TMT of the radiation part. In other words, it is possible to accomplish all of the abovementioned effects. This means that the operation condition of the thermal-cracking apparatus of the present invention can be suitably designed for the particularly aimed effect.

As described above, according to the present invention, it is possible to obtain various characteristics or performances by combining various operation conditions on the basis of catalytic activity, heat transfer characteristic and anti-coking property of the catalyst.

In one characteristic or performance, according to the present invention, it is possible to shorten a residence time in the tube of the radiation part. For example, when comparing a thermal-cracking apparatus packed with no catalyst and a thermal-cracking apparatus of the present invention with 30% by volume of the tube of the radiation part being packed with the catalyst, it is possible to shorten the residence time of the reaction stream in the tube of the radiation part by 20 to 40% and about 30% respectively in such a condition that conversion rate of supplied hydrocarbon and yield of light olefin are maintained to be equal and in such a condition that the COT of the reaction stream at the outlet of the radiation part is maintained to be equal. This means that the efficiency of heat transfer from the tube of the radiation part to the reaction stream is higher in the thermal-cracking method of the present invention and therefore a length of the tube of the radiation part can be more shorten or a liquid hourly space velocity (LHSV) of the reaction stream can be raised.

In another characteristic or performance, according to the present invention, it is possible to lower TMT. For example, the same performance as the conversion rate of hydrocarbons and yield of light olefins obtained in such an operation condition that the TMT is at the level of 1060° C. so as to maintain the COT of the reaction stream at the outlet of the radiation part packed with no catalyst to 800° C., can be obtained in the more relieved operation condition in the thermal-cracking method of the present invention. In other words, such performance can be an operation condition in that the TMT is at the level of 1000° C. so as to maintain the COT of the reaction stream at the outlet of the radiation part packed with no catalyst to 800° C.

As such, shortening of the residence time of the reaction stream or the operation in the relieved operation condition allows to increase processing capacity per unit time and reduce fuel consumption as well as to extend decoking interval.

Also, in the thermal-cracking apparatus of the present invention, deterioration of the performance is not largely generated even after continuous usage and decoking process. In other words, the thermal-cracking apparatus of the present invention has a high ability of maintaining the performance. For example, with the thermal-cracking method of the present invention, a performance loss indicated by the conversion rate of hydrocarbon and the yield of light olefin is maintained up to 1 to 5% even after two to five times repetition of continuous operation of the thermal-cracking reaction for 120 hours with the COT of the reaction stream at the outlet of the radiation part being 800° C. and then decoking at 800° C. in the presence of air and steam.

Therefore, such test result in the pilot plant shows that it is highly possible for the thermal-cracking method to be applied to a plant for the actual mass production with industrial scale and economy.

With such excellent performance of the present invention, the thermal-cracking apparatus of the present invention can process high concentration of hydrocarbon feedstocks and also can process with fast LHSV. For example, the thermal-cracking apparatus of the present invention can be operated at the steam/hydrocarbon weight ratio of 0.4 to 0.6 with the LHSV of the reaction stream of 1 to 20 $hr^{-1}$ when the temperature of thermal-cracking in the radiation part is 750 to 950° C.

The yield of $C_4$ or lower light olefin produced by operation at the initial condition, in that the TMT is set from 1060° C. to 1000° C., the residence time of hydrocarbon is set from 0.1 second to 0.07 second and the LHSV of hydrocarbon is set from 10 $hr^{-1}$ to 13 $hr^{-1}$ to maintain the COT of the racked gas at the outlet of the radiation part to 800° C., is 43.5% by weight and the yield after continuous three cycles of 120 hour-operation is 41.9% by weight. The thermal-cracking of the present invention is therefore characterized in that the loss of the performance is maintained up to 1 to 5%.

BRIEF DESCRIPTION OF THE DRAWINGS

The above and other objects, features and advantages of the present invention will become apparent from the following description of preferred embodiments given in conjunction with the accompanying drawings, in which.

BEST MODE FOR CARRYING OUT THE INVENTION

Figure 1:
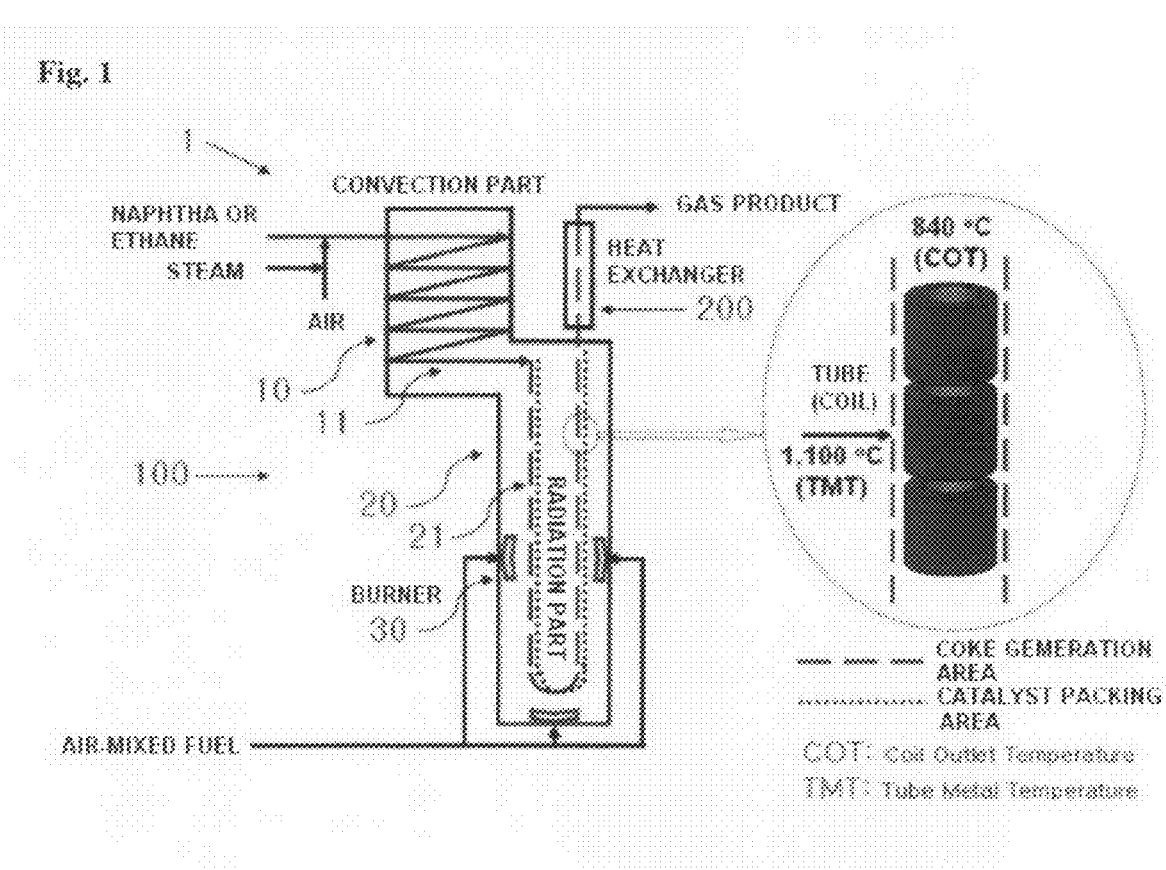
FIG. 1 is a schematic diagram of a tube type furnace packed with a specific catalyst, used in a method of thermal-cracking of hydrocarbon according to an embodiment of the present invention.
Figure 2:
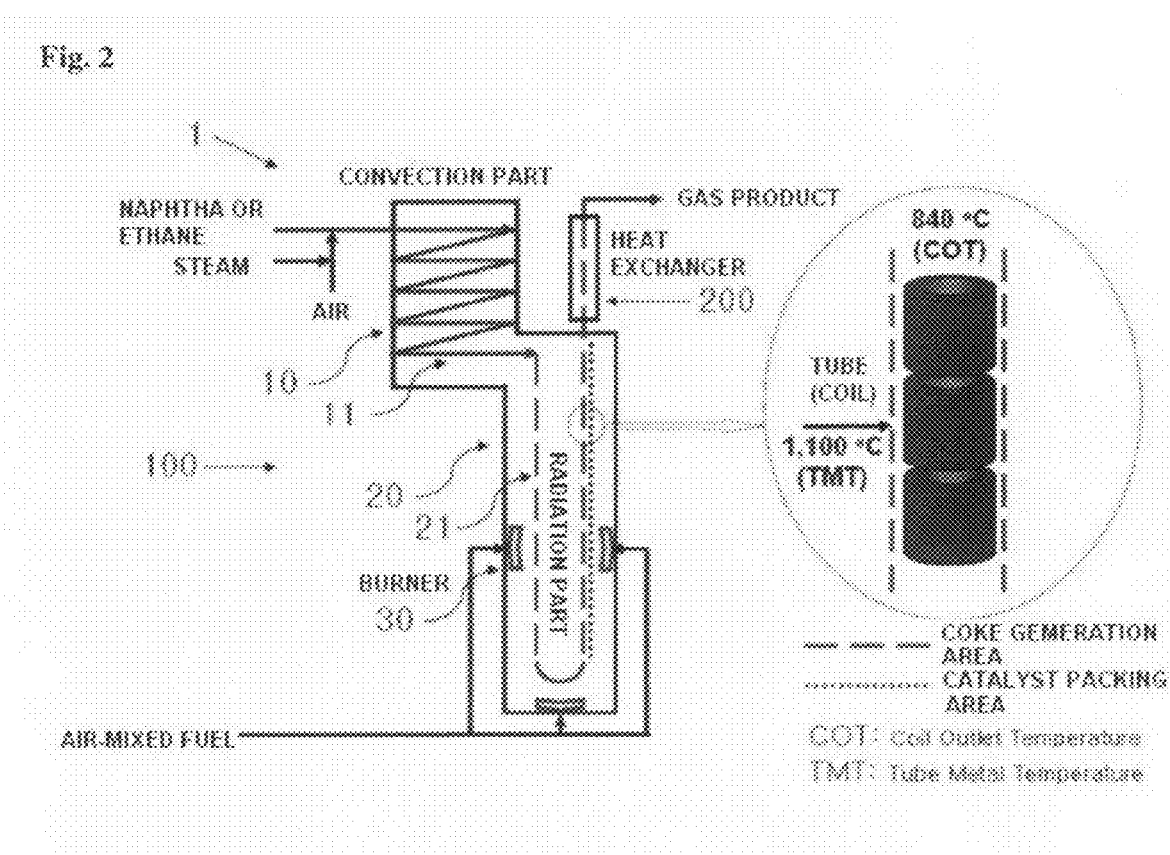
FIG. 2 is a schematic diagram of a tube type furnace packed with a specific catalyst, used in a method of thermal-cracking of hydrocarbon according to another embodiment of the present invention.
Figure 3:
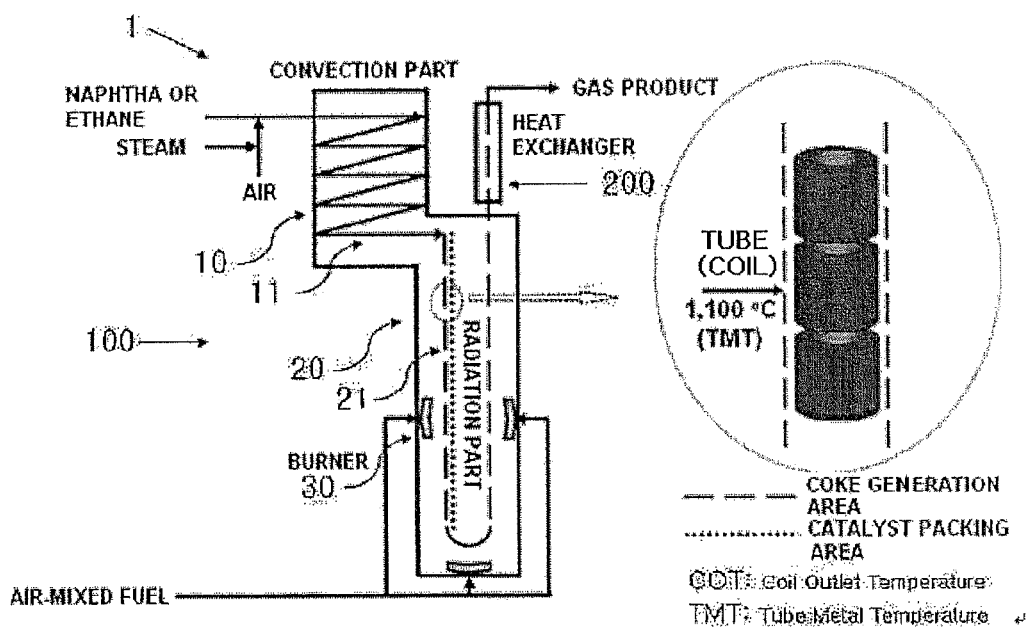
FIG. 3 is a schematic diagram of a tube type furnace packed with a specific catalyst, used in a method of thermal-cracking of hydrocarbon according to further another embodiment of the present invention.

Practical and presently preferred embodiments of the present invention are illustrative as shown in the following Examples.

However, it will be appreciated that those skilled in the art, on consideration of this disclosure, may make modifications and improvements within the spirit and scope of the present invention.

CATALYST PREPARATION EXAMPLE 1

In water was dissolved 2.68 g of titanium isopropoxide, followed by stirring with dropping nitric acid until the solution became transparent. To the solution were added 12.35 g of zirconium nitrate hydrate and 0.24 g of chromium nitrate hydrate to prepare a mixed aqueous solution. With slowly dropping ammonia water, pH of the aqueous solution was regulated to pH 8. After coprecipitation, the aqueous solution was reflux-heated for 12 hours. The coprecipitated aqueous solution was filtered and washed with water. A catalyst was separated and dried in a drier. The dried catalyst was heated at 800° C. for 6 hours in the presence of air for calcination.

The catalyst prepared above had the composition of $CrZr_{83.3}Ti_{16.7}O_x$.

CATALYST PREPARATION EXAMPLE 2

An experiment was performed by the same manner as described in preparation example 1, except that calcinations was induced at 1200° C.

CATALYST PREPARATION EXAMPLE 3

The catalyst prepared in preparation example 1 proceeded to normal hexane contacting steam cracking for 5 hours under the same condition as described in the following example and then recovered and regenerated by burning coke at 800° C. for 6 hours in the presence of air.

CATALYST PREPARATION EXAMPLE 4

The catalyst powder prepared in Catalyst Preparation Example 1 was mixed with silicon carbide powder prepared in the following Catalyst Preparation Comparative Example 2 and then vacuum sintered. The sintered catalyst had a composition of 5, 10 and 15% by weight, based on the weight of silicon carbide, of $CrZr_{83.3}Ti_{16.7}O_x$.

CATALYST PREPARATION COMPARATIVE EXAMPLE 1

500 μm sized α-alumina with 99.5% purity was used as a catalyst.

CATALYST PREPARATION COMPARATIVE EXAMPLE 2

500 μm sized silicon carbide with 99.5% purity was used as a catalyst.

EXAMPLES 1 to 4 and COMPARATIVE EXAMPLES 1 and 2

Catalysts prepared in the above Catalyst Preparation Examples 1 to 4 and Catalyst Preparation Comparative Example 1 and 2 were used for laboratory hydrocarbon steam cracking as follows.

Normal hexane was used as hydrocarbon feedstock. Quartz tube with ¼" outside diameter was packed with each catalyst by 5 cm in height. The reaction temperature was maintained at 750° C. Hexane and water were used in a ratio of 2:1 (by weight) and the flow rate (LHSV) of normal hexane was set to 5 $hr^{-1}$, based on a tube volume excluding the volume packed with the catalyst. Hexane and water were injected by using a syringe pump. The hexane and water were vaporized in a vaporizer at 400° C. and at 500° C. respectively. The two gases were well mixed and contacted with the catalyst layer. The degradation product from the reactor proceeded to gas chromatography for quantitative analysis. The yield of the degradation product was calculated by the following Equation 1.

Yield of product (wt %)=weight of product/weight of injected hexane×100     [Equation 1]

CATALYST PREPARATION EXAMPLE 5

The catalyst powder prepared in Catalyst Preparation Example 1 was mixed with silicon carbide powder and then vacuum sintered. The sintered catalyst had a composition of 10% by weight, based on the weight of silicon carbide, of $CrZr_{83.3}Ti_{16.7}O_x$ and a density of 1.34 g/cm$^3$.

CATALYST PREPARATION COMPARATIVE EXAMPLE 3

Silicon carbide with 99.5% purity and 2.6 g/cm$^3$ density was used as a catalyst.

EXAMPLE 5 and COMPARATIVE EXAMPLES 3 and 4

Catalysts prepared in the above Catalyst Preparation Example 5 and Catalyst Preparation Comparative Example 3 were used for hydrocarbon steam cracking in a pilot plant as follows, and a result of Catalyst Preparation Comparative Example 4 was also illustrative for comparing the performance thereof with the hydrocarbon steam cracking without using the catalyst. At this time, naphthas were used as hydrocarbon feedstocks for steam cracking and the compositions and physical properties of naphthas are summarized in Table 1 below.

TABLE 1

| Physical property | | | | | | |
|---|---|---|---|---|---|---|
| Density (g/cc) | Initial boiling point (° C.) | Terminal boiling point (° C.) | Composition (wt %) | | | |
| | | | n-paraffin | I-paraffin | naphthene | Aromatics |
| 0.675 | 30.9 | 160.7 | 39.5 | 38.9 | 15.3 | 6.3 |

Naphthas and water were injected into a reaction apparatus by using a quantitative pump. At this time, naphthas and water were used in a ratio of 2:1 (by weight) and the flow rate (LHSV) of naphthas was set to 10 hr$^{-1}$. Naphthas and water which had been injected into the reaction apparatus were mixed via a vaporizer, heated to 550 C in a primary preheater and then to 650° C. in a secondary preheater, and injected into a reactor (length: 300 cm, diameter: 4.3 cm) packed with a catalyst.

The reactor was heated by an electric furnace. Mixtures of steam and naphthas that had passed through the secondary preheater were subjected to contact cracking in the reactor. At this time, a reactor outlet temperature (a reaction temperature) was maintained at a desired temperature. While passing through two condensers serially connected, water and heavy oils were condensed into a liquid phase and recovered, and vapor mixtures were discharged out after online gas chromatography. The naphtha contact cracking was performed for 120 hours and then the catalyst was regenerated by burning coke in the in the presence of steam and air. The yield of ethylene was calculated by the following Equation 2. The yields of other products (propylene) were also calculated in the same manner. Also, averages for 120 hours are used for each data.

$$\text{Yield of ethylene (wt \%)} = \text{weight of produced ethylene/weight of injected naphtha} \times 100 \quad \text{[Equation 2]}$$

TABLE 2

| | | Catalyst composition | Yield of product (wt %) | | | Conversion rate (wt %) |
|---|---|---|---|---|---|---|
| | | | Ethylene | Propylene | Ethylene + Propylene | |
| Examples | 1 | $CrZr_{83.3}Ti_{16.7}O_x$ | 22.4 | 20.2 | 44.6 | 75.1 |
| | 2 | $CrZr_{83.3}Ti_{16.7}O_x$ | 24.1 | 18.1 | 42.2 | 67.7 |
| | 3 | $CrZr_{83.3}Ti_{16.7}O_x$ | 23.9 | 19.6 | 43.5 | 72.7 |
| | 4 | 5% $CrZr_{83.3}Ti_{16.7}O_x$ + SiC | 23.0 | 15.6 | 39.5 | 60.2 |
| | | 10% $CrZr_{83.3}Ti_{16.7}O_x$ + SiC | 23.9 | 15.6 | 39.5 | 62.2 |
| | | 15% $CrZr_{83.3}Ti_{16.7}O_x$ + SiC | 24.9 | 16.0 | 40.8 | 64.1 |
| Comparative Examples | 1 | α-alumina | 22.3 | 14.3 | 36.6 | 60.4 |
| | 2 | SiC | 21.3 | 13.7 | 35.1 | 55.9 |

As shown in Table 2, the catalyst of Example 1, which is an oxide catalyst containing Cr, Zr and Ti, a transition metal, prepared by firing at 800° C., could increase the conversion rate of normal hexane degradation approximately 15 to 20% by weight and the yield of olefin approximately 8 to 9% by weight, compared with those of α-alumina and Sic with very small surface area and no micropore volume of Comparative Examples 1 and 2 which exhibited no catalytic activity, owing to the generated catalytic active site of hydrocarbon steam cracking resulted from the complicated oxide structure of Cr, Zr and Ti. The catalyst of the invention, an oxide catalyst containing Cr, Zr and Ti, was also confirmed to be every effective in the production of light olefin, particularly propylene, by hydrocarbon contact cracking.

In general, the reaction temperature during hydrocarbon steam cracking is 800° C. However, there is a chance for the catalyst to be exposed on a higher temperature locally resulted from hot-spot generated during burning for eliminating coke generated on the surface of a catalyst or inside wall of a reactor. So, a catalyst having excellent thermo-stability is required to keep its catalytic activity even at higher temperature more than 1000° C. for successful hydrocarbon cracking. The catalyst containing Cr, Zr and Ti of example 2 which was prepared by calcining at 1200° C. exhibited reduced catalytic activity for hexane degradation and lower olefin yield approximately 2.5 weight %, compared with the catalyst of example 1, but still exhibited higher catalytic activity than α-alumina and Sic with very small surface area and no micropore volume of Comparative Examples 1 and 2 which exhibited no catalytic activity.

The catalyst of example 3, regenerated after burning the coke generated on the surface of the catalyst at high temperature upon completion of hydrocarbon steam cracking, maintained high catalytic activity. That is, the oxide catalyst containing Cr, Zr and Ti is very stable at high temperature in the range of 800 to 1200° C. and maintains excellent catalytic activity after the regeneration.

Also, the hybrid catalyst of Example 4, which is a mixture of an oxide catalyst component containing $CrZr_{83.3}Ti_{16.7}O_x$ and silicon carbide, a carrier, could increase the yield of light olefin (ethylene, propylene), compared with that of silicon carbide of Comparative Example 2 which has no catalytic active site. Increase in the content of $CrZr_{83.3}Ti_{16.7}O_x$ results in large increase in the yield of light olefin. When the content of $CrZr_{83.3}Ti_{16.7}O_x$ is increased to 15% by weight, the yield of light olefin is increased 5.8% by weight. The hybrid catalysts of above Examples exhibited high catalytic activity and selectivity even though fired at a high temperature of more than 1200° C. Particularly, the catalyst prepared in Catalyst Preparation Example 4 and used in Example 4 exhibited almost no loss of the catalytic activity and excellent light olefin selectivity.

cracking to the reactant except for packed volume at a temperature of 800° C. explains well relatively reduced yield of light olefin. On the contrary, comparison of reaction activity of the hybrid catalyst of Example 5 with Comparative Example 5 shows increase in the light olefin yield due to catalytic reaction effect, unlike Comparative Example 5. According to the method of the present invention, the TMT of Example 5 shows heat transfer effect of at least 60° C. in the same light olefin yield, compared with Comparative Example 5.

The ratio of methane/propylene and the ratio of ethylene/propylene are indexes not only for cracking process severity but also for light olefin selectivity.

As shown in Table 3, when cracking was performed at the temperature of 800° C., the ratio of ethylene/propylene in Example 5 was 1.7 and the ratios of ethylene/propylene in Comparative Examples 4 and 5 were 2.0 and 2.2 respectively. That is, the ratio of ethylene/propylene in the hybrid catalyst of Example 5 is lower than that in catalysts of Comparative Examples 4 and 5, suggesting that the hybrid catalyst of the present invention is effective in increasing propylene selectivity. Also, when the TMT at the same outside surface of the tube is 1025° C. and 980° C. respectively, light olefin yield was higher by 3.6 to 3.7% by weight than that in Comparative Example 5. This means that the production amount of light olefin can be increased at the same amount of heat source for heating the cracking reactor. In other words, the fuel consumption can be reduced to produce the same amount of light olefin or the more amount of light olefin can be produced at the same fuel consumption.

More production of propylene at the same methane production may indicate increase in propylene selectivity. Low ethylene/propylene ratio also indicates that the catalyst is friendly to produce propylene. When considering Comparative Example 4 in which silicon carbide has no active site and thus thermal-cracking alone is generated, the hybrid catalyst of Example 5 is effective to increase the yields of ethylene and propylene and particularly effective to increase the propylene selectivity.

TABLE 3

| | Reaction temperature (° C.) | Temperature of outer surface of tube (° C.) | Yield of product (wt %) | | | | Ratio of | |
| --- | --- | --- | --- | --- | --- | --- | --- | --- |
| | | | Methane | Ethylene | Propylene | Butadiene | Ethylene + Propylene | Ethylene/ Propylene |
| Example 5 | 800 | 1001 | 15.8 | 27.1 | 16.4 | 4.7 | 43.5 | 1.7 |
| Comparative Example 4 | 800 | 1054 | 16.0 | 26.8 | 13.3 | 3.8 | 40.2 | 2.0 |
| Comparative Example 5 | 800 | 1064 | 16.9 | 29.9 | 13.6 | 3.9 | 43.5 | 2.2 |
| Example 5 | 820 | 1027 | 19.0 | 31.8 | 14.4 | 4.5 | 46.3 | 2.2 |
| Comparative Example 5 | 780 | 1022 | 14.7 | 27.2 | 15.5 | 4.0 | 42.7 | 1.8 |
| Example 5 | 781 | 975 | 14.2 | 25.4 | 17.3 | 4.3 | 42.6 | 1.5 |
| Comparative Example 5 | 760 | 983 | 12.2 | 23.0 | 15.9 | 3.5 | 38.9 | 1.4 |

As shown in Table 3, the hybrid catalyst of Example 5, which is a mixture of an oxide catalyst component containing $CrZr_{83.3}Ti_{16.7}O_x$ and silicon carbide, a carrier, could increase the yield of light olefin (ethylene, propylene) approximately 3% by weight, compared with that of silicon carbide of Comparative Example 4 which has no catalytic active site. Also, comparison of Comparative Example 5, which is a steam cracking in a vacant tube packed with no catalyst, with Comparative Example 4 shows that reduced time for contact Deposition of coke onto the reactor and catalyst surface is inevitable during high temperature naphtha cracking. In general, the reaction temperature during hydrocarbon steam cracking is 800° C. However, there is a chance for the catalyst to be exposed on a higher temperature locally resulted from hot-spot generated during burning for eliminating coke generated on the surface of a catalyst or inside wall of a reactor. So, a catalyst having excellent thermo-stability is required to keep its catalytic activity even at higher temperature more than 1000° C. for successful hydrocarbon cracking. The hybrid catalyst of Example 5 recovered most of its catalytic performance, had no external thermal/physical deformation and maintained its initial mechanical strength after regenerated by burning the coke generated on the surface of the catalyst at high temperature upon completion of naphtha cracking.

In other words, the hybrid catalyst of Example 5 was confirmed to be very stable at low temperature of up to 1000° C. and at high temperature of at least 1200° C., exhibit low inactivation due to the coke and maintain excellent catalytic activity.

INDUSTRIAL APPLICABILITY

As apparent from the above description, the hydrocarbon steam cracking according to the present invention can accomplish high yield of light olefin, reduction in fuel consumption due to excellent heat transfer effect, reduction in production of coke deposited onto the inside wall of the tube and extension of interval of decoking operation, by packing specific catalyst having excellent thermal/mechanical stability, low inactivation due to the coke and increased selectivity and yield of light olefin, in the tube of the radiation part of the tube type furnace.

Those skilled in the art will appreciate that the conceptions and specific embodiments disclosed in the foregoing description may be readily utilized as a basis for modifying or designing other embodiments for performing the same purposes of the present invention. Those skilled in the art will also appreciate that such equivalent embodiments do not depart from the spirit and scope of the invention as set forth in the appended claims.

The invention claimed is:

1. A thermal-cracking method of hydrocarbon using a hydrocarbon thermal-cracking apparatus comprising a tube furnace including a radiation part for thermally cracking hydrocarbon feedstocks supplied together with steam and a convection part, wherein the method comprises the step of:
   mixing an oxide catalyst with a carrier or supporting the oxide catalyst on the carrier, wherein the oxide catalyst is represented by $CrZr_jA_kO_x$, wherein $0.5 \leq j \leq 120$ and $0 \leq k \leq 50$, A is a transition metal, and x is a number corresponding to the atomic values of Cr, Zr, and A and the numbers of j and k, to form a hydrocarbon thermal-cracking catalyst,
   packing the hydrocarbon thermal-cracking catalyst in some or entire area of a tube placed in the radiation part of the tube furnace in a shape of rasching ring, partition ring, lessing ring or sponge,
   wherein the hydrocarbon thermal-cracking catalyst has a density of 0.5 to 3.5 g/cm$^3$, a surface area of up to 50 m$^2$/g and a compressive strength of at least 1000N, and
   wherein a heat transfer efficiency of the method is such that when a cracked gas temperature is set to at least 800° C. at an outlet of the radiation part of the tube furnace, a tube metal temperature is lowered to at least 60° C. at the outlet of the radiation part of the tube furnace, compared with when the hydrocarbon catalyst is not packed.

2. The method as set forth in claim 1, wherein the amount of the oxide catalyst is in a range of 0.5 to 30% by weight, based on total weight of the oxide catalyst and the carrier.

3. The method as set forth in claim 1, wherein the A of the oxide catalyst is one or more compounds selected from the group consisting of Ti, Nb, Mo, V, Co, Ni, W, Fe and rare earth metals.

4. The method as set forth in claim 1, wherein the A of the oxide is Ti.

5. The method as set forth in claim 1, wherein the carrier is selected from the group consisting of alpha-alumina, silica, silica-alumina, zirconium oxide, magnesium oxide, magnesium aluminate, calcium aluminate, silicon carbide, aluminum titanate and zeolite.

6. The method as set forth in claim 1, wherein the carrier is silicon carbide.

7. The method as set forth in claim 1, wherein the hydrocarbon thermal-cracking catalyst is formed in such a manner that powder of the oxide catalyst and powder of the carrier are mixed and sintered, or that the carrier is dipped with an aqueous precursor solution of the oxide catalyst and then fired.

8. The method as set forth in claim 1, wherein the method can shorten a residence time of the supplied hydrocarbon in the tube of the radiation part 20 to 40% compared with when packed with no hydrocarbon thermal-cracking catalyst, in such a condition that conversion rate of the supplied hydrocarbon and yield of produced C4 or lower light olefin when 30% of the tube of the radiation part is packed with the hydrocarbon thermal-cracking catalyst are maintained the same as when packed with no hydrocarbon thermal-cracking catalyst.

9. The method as set forth in claim 1, wherein the method can obtain the same performance as conversion rate of the supplied hydrocarbon and yield of produced C4 or lower light olefin obtained when the tube metal temperature at the outlet of the radiation part packed with no hydrocarbon thermal-cracking catalyst is 1060° C., in such a condition that the tube metal temperature at the outlet of the radiation part is up to 1000° C.

10. The method as set forth in claim 1, wherein a loss of the performance indicated by the conversion rate of the hydrocarbon and the yield of C4 or lower light olefin is up to 1 to 5% after two to five times repetition of performing continuously the thermal-cracking for 120 hours in the state that the cracked gas temperature is 800° C. at the outlet of the radiation part and then performing decoking operation in the presence of steam and air.

11. The method as set forth in claim 1, wherein the method is operated at the steam/hydrocarbon weight ratio of 0.3 to 1.0 with the liquid hourly space velocity of hydrocarbon of 1 to 20 hr$^{-1}$ when the cracked gas temperature is 750 to 950° C. at the outlet of the radiation part.

* * * * *